United States Patent
Beatty et al.

(10) Patent No.: US 7,791,728 B2
(45) Date of Patent: Sep. 7, 2010

(54) SYSTEM FOR OPTICALLY ANALYZING A SUBSTANCE WITH A SELECTED SINGLE-WAVELENGTH

(75) Inventors: Christopher C. Beatty, Albany, OR (US); Philip Harding, Albany, OR (US); Christie Dudenhoefer, Corvallis, OR (US); Charles Otis, Corvalis, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 831 days.

(21) Appl. No.: 11/201,983

(22) Filed: Aug. 11, 2005

(65) Prior Publication Data

US 2007/0037272 A1   Feb. 15, 2007

(51) Int. Cl.
G01N 21/00 (2006.01)
(52) U.S. Cl. .................. 356/440; 356/246; 356/411
(58) Field of Classification Search ............ 356/432, 356/39–42, 244–246, 426–428, 435–436, 356/440–442
See application file for complete search history.

(56) References Cited

U.S. PATENT DOCUMENTS

| | | | | |
|---|---|---|---|---|
| 3,910,701 | A * | 10/1975 | Henderson et al. | 356/39 |
| 4,234,540 | A | 11/1980 | Ginsberg et al. | |
| 4,406,547 | A * | 9/1983 | Aihara | 356/414 |
| 5,222,495 | A * | 6/1993 | Clarke et al. | 600/322 |
| 6,339,472 | B1 * | 1/2002 | Hafeman et al. | 356/433 |
| 6,531,095 | B2 * | 3/2003 | Hammer et al. | 422/64 |
| 6,602,702 | B1 | 8/2003 | McDevitt et al. | |
| 6,713,298 | B2 | 3/2004 | McDevitt et al. | |
| 6,719,682 | B2 | 4/2004 | Kellogg et al. | |
| 6,812,456 | B2 | 11/2004 | Andersson et al. | |
| 2002/0028158 | A1 * | 3/2002 | Wardlaw | 422/82.05 |
| 2002/0058273 | A1 | 5/2002 | Shipwash | |
| 2002/0092767 | A1 | 7/2002 | Bjornson | |
| 2003/0066959 | A1 | 4/2003 | Andersson et al. | |
| 2003/0104470 | A1 | 6/2003 | Fors et al. | |
| 2003/0186228 | A1 | 10/2003 | McDevitt et al. | |
| 2003/0195106 | A1 | 10/2003 | Kellogg et al. | |
| 2004/0029259 | A1 | 2/2004 | McDevitt et al. | |
| 2004/0053322 | A1 | 3/2004 | McDevitt et al. | |
| 2004/0063168 | A1 * | 4/2004 | Wiles et al. | 435/29 |
| 2004/0089616 | A1 | 5/2004 | Kellogg et al. | |
| 2004/0101191 | A1 | 5/2004 | Seul et al. | |
| 2004/0191125 | A1 | 9/2004 | Kellogg et al. | |
| 2004/0219523 | A1 | 11/2004 | Stanton et al. | |
| 2005/0014179 | A1 | 1/2005 | Karlsson et al. | |
| 2005/0059062 | A1 * | 3/2005 | Kaiser | 435/6 |
| 2005/0083522 | A1 | 4/2005 | Aravanis et al. | |
| 2005/0089993 | A1 | 4/2005 | Boccazzi et al. | |
| 2005/0100937 | A1 | 5/2005 | Holmes | |

(Continued)

FOREIGN PATENT DOCUMENTS

EP   1124128 A2   8/2001

(Continued)

*Primary Examiner*—Tarifur Chowdhury
*Assistant Examiner*—Tara S Pajoohi

(57) ABSTRACT

A microfluidic analysis system for optically analyzing a substance includes a light source having a plurality of selectable single-wavelength light sources, a substance presentation member optically coupled to the light source, and an optical detection system associated with the substance presentation member.

13 Claims, 9 Drawing Sheets

U.S. PATENT DOCUMENTS

| | | | |
|---|---|---|---|
| 2005/0101841 A9 | 5/2005 | Kaylor et al. | |
| 2005/0106746 A1* | 5/2005 | Shinn et al. | 436/164 |
| 2005/0112784 A1 | 5/2005 | Yguerabide et al. | |
| 2007/0232874 A1* | 10/2007 | Ince | 600/320 |
| 2008/0055593 A1* | 3/2008 | Fox | 356/244 |

FOREIGN PATENT DOCUMENTS

| | | |
|---|---|---|
| JP | 11037932 AA | 2/1999 |
| JP | 2003021594 AA | 1/2003 |

* cited by examiner

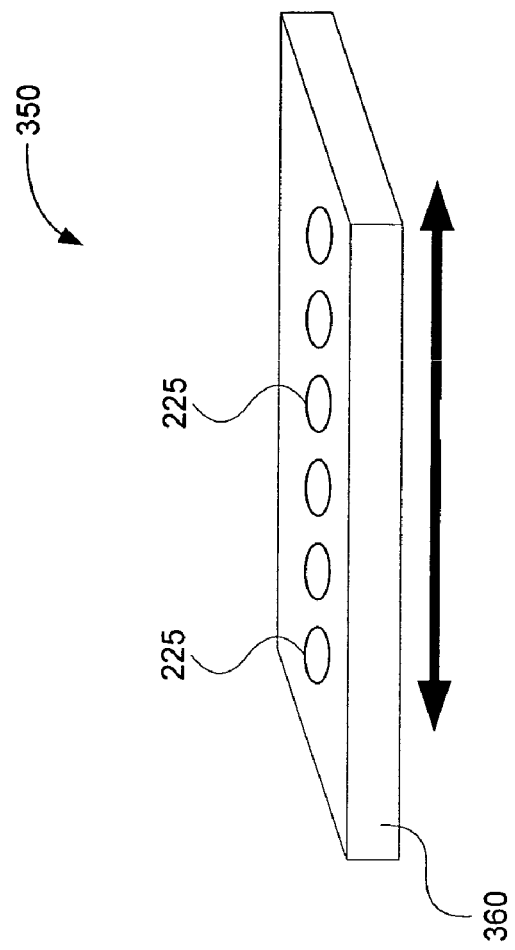
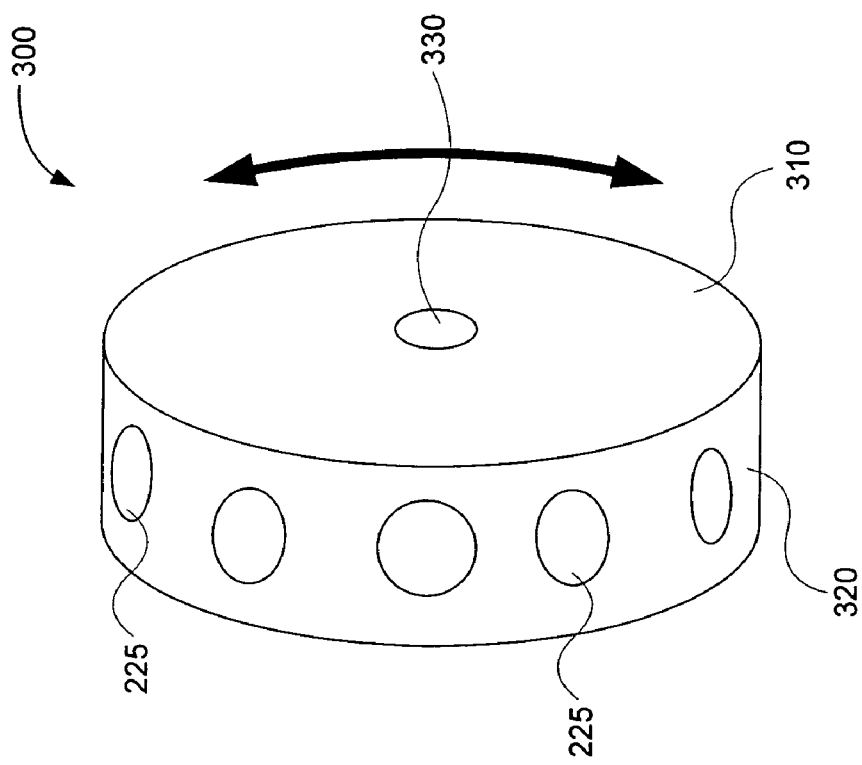
Fig. 3b
Fig. 3a

SYSTEM FOR OPTICALLY ANALYZING A SUBSTANCE WITH A SELECTED SINGLE-WAVELENGTH

BACKGROUND

Recent trends in biomedical diagnostics and drug discovery suggest a rapid growth in the use of high speed and high throughput chemical detection, chemical screening, and compound synthesis. Several systems make use of instruments that require large sample volumes, are difficult to transport, and are prohibitively expensive. Efforts are being directed to accelerate drug delivery and therapeutics, contain high health care costs, and provide decentralized biomedical diagnostics, such as diagnostics for point of care, and other future technologies. Such efforts frequently focus on increased miniaturization, integration, and automation of fluid analysis systems.

Fluid analysis systems traditionally use a number of components, including a light source, a wavelength selection system, a sample presentation system, and a detection system to analyze a patient's fluids. However, each of these components sometimes add prohibitive cost to the overall fluid analysis system, thereby limiting the ownership of traditional fluid analysis systems to large clinics and laboratories.

SUMMARY

According to one exemplary embodiment, a system for optically analyzing a substance includes a light source having a plurality of selectable single-wavelength light sources coupled thereto, a substance presentation member optically coupled to the light source, and an optical detection system associated with the substance presentation member.

Additionally, according to another exemplary embodiment, a method for using a light source carousel having a plurality of selectable single-wavelength light sources coupled thereto includes selecting a desired single-wavelength light source from the plurality of selectable single-wavelength light sources, illuminating an analyte-containing region with the desired single-wavelength light source, and detecting a wavelength associated with the illuminated analyte-containing region.

BRIEF DESCRIPTION OF THE DRAWINGS

The accompanying drawings illustrate various embodiments of the present apparatus and method and are a part of the specification. The illustrated embodiments are merely examples of the present apparatus and method and do not limit the scope of the disclosure.

FIGS. 3a and 3b illustrate perspective views of various configurations of light source and wavelength selection systems, according to various exemplary embodiments.

Throughout the drawings, identical reference numbers designate similar, but not necessarily identical, elements.

DETAILED DESCRIPTION

Figure 1:
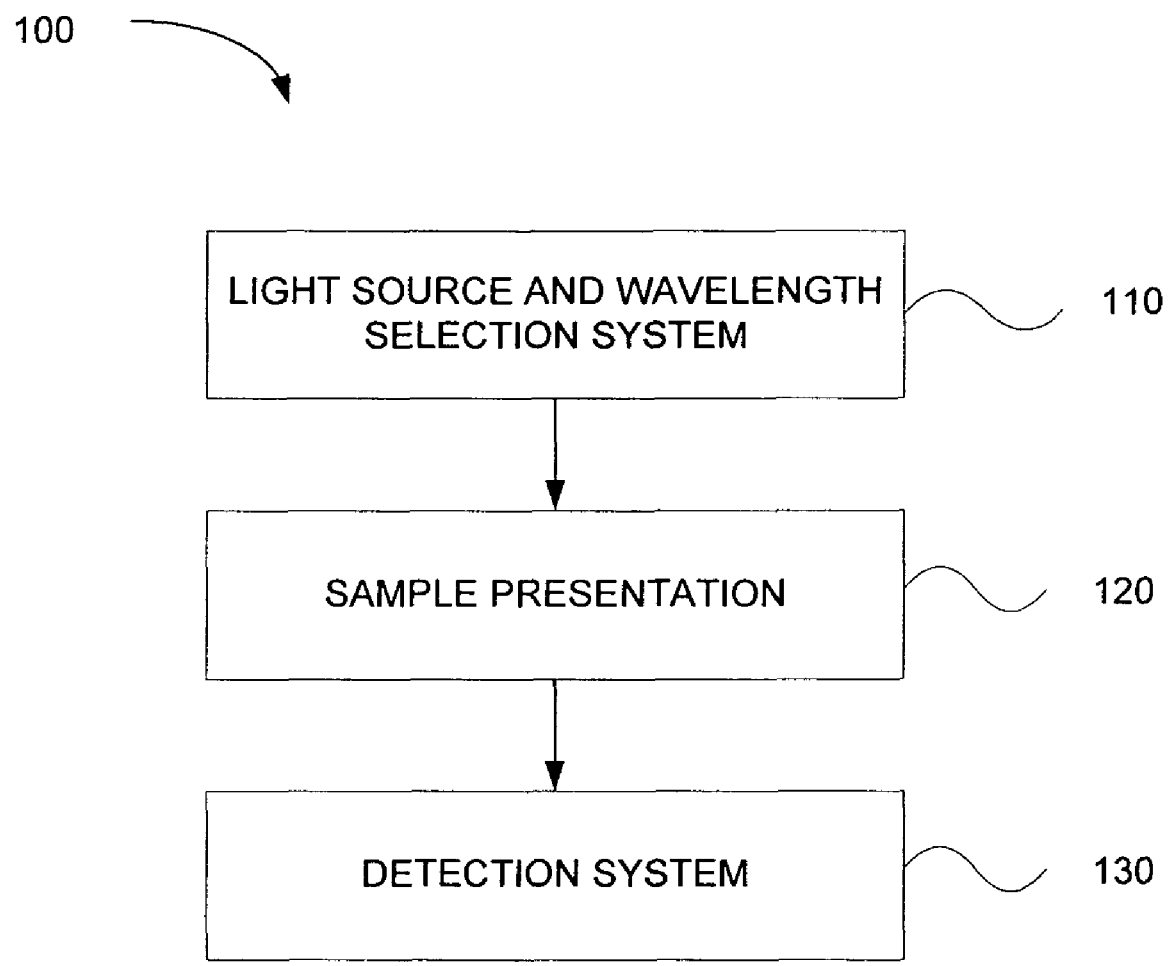
FIG. 1 is a simple block diagram illustrating the components of a fluid analysis system, according to one exemplary embodiment.

The present specification discloses an exemplary system and method for completing an optical analysis on a millimeter or microliter scale volume of fluid. More specifically, according to one exemplary embodiment, a multi-wavelength selector structure having multiple single-wavelength light sources such as light emitting diodes (LEDs) or lasers is described. Numerous details of the multi-wavelength selector structure having multiple light sources, as well as an exemplary system that may incorporate the multi-wavelength selector structure will be provided below.

Before particular embodiments of the present system and method are disclosed and described, it is to be understood that the present system and method are not limited to the particular process and materials disclosed herein as such may vary to some degree. It is also to be understood that the terminology used herein is used for the purpose of describing particular embodiments only and is not intended to be limiting, as the scope of the present system and method will be defined only by the appended claims and equivalents thereof. In describing and claiming the present exemplary system and method, the following terminology will be used.

The singular forms "a," "an," and "the" include plural referents unless the context clearly dictates otherwise. Thus, for example, reference to "a light source" includes reference to one or more of such light sources.

As used herein, the term "light" will be meant to be understood as any electromagnetic radiation with a wavelength ranging from infrared to ultraviolet.

Additionally, as used herein, and in the appended claims, the term "analyte" shall be interpreted broadly as referring to any compound or substance chosen to undergo analysis by the present exemplary system and method. Additionally, as used herein, the term "analyte" shall also be interpreted broadly as including any number of analyte reaction chemistries configured to enhance analysis by the present system and method, regardless of whether the analyte reaction chemistries include the originally identified analyte.

Furthermore, as used in the present specification, and in the appended claims, the term "single-wavelength light source" shall be interpreted broadly to include any number of light sources having a seemingly narrow wavelength spectrum. Particularly, as used herein, a single-wavelength light source shall include any light source that, while technically polychromatic, is sufficiently narrow with respect to an analyte or chromophore absorption or emission spectrum to provide a quantifiable chemical analysis. The seemingly narrow wavelength spectrum of a light emitting diode (LED) shall be interpreted herein as a single-wavelength light source.

In the following description, for purposes of explanation, numerous specific details are set forth in order to provide a thorough understanding of the present multi-wavelength selector structure having multiple light sources. It will be apparent, however, to one skilled in the art that the present method and apparatus may be practiced without these specific details. Reference in the specification to "one embodiment"

or "an embodiment" means that a particular feature, structure, or characteristic described in connection with the embodiment is included in at least one embodiment. The appearance of the phrase "in one embodiment" in various places in the specification are not necessarily all referring to the same embodiment.

Exemplary System

A fluid analysis system (100) incorporating a multi-wavelength selector structure with multiple single-wavelength light sources is illustrated in FIG. 1, according to one exemplary embodiment. As illustrated in FIG. 1, the present fluid analysis system (100) includes a single unit configured to function as a light source and wavelength selection system (110), a sample presentation system (120), and a signal detection system (130). As mentioned previously, prior art fluid analysis systems include multiple complex and high priced components such as independent light sources such as xenon strobes or tungsten lamps, a wavelength selection system such as filters or monochromators, an analyte sample presentation system such as a glass or polymer cuvette or a well plate that accommodates an analyte test volume of approximately 200 to 10,000 microliters, and a sample detection system including expensive photomultiplier tubes. According to one exemplary embodiment, the present combination light source and wavelength selection system effectively eliminates the expensive filters or monochromaters incorporated by traditional fluid analysis systems, thereby reducing the overall cost of the present fluid analysis system (100), while efficiently and elegantly providing desired wavelengths for analysis. Further details of the present fluid analysis system (100) will be provided below with reference to FIGS. 3 through 8.

Figure 2A:
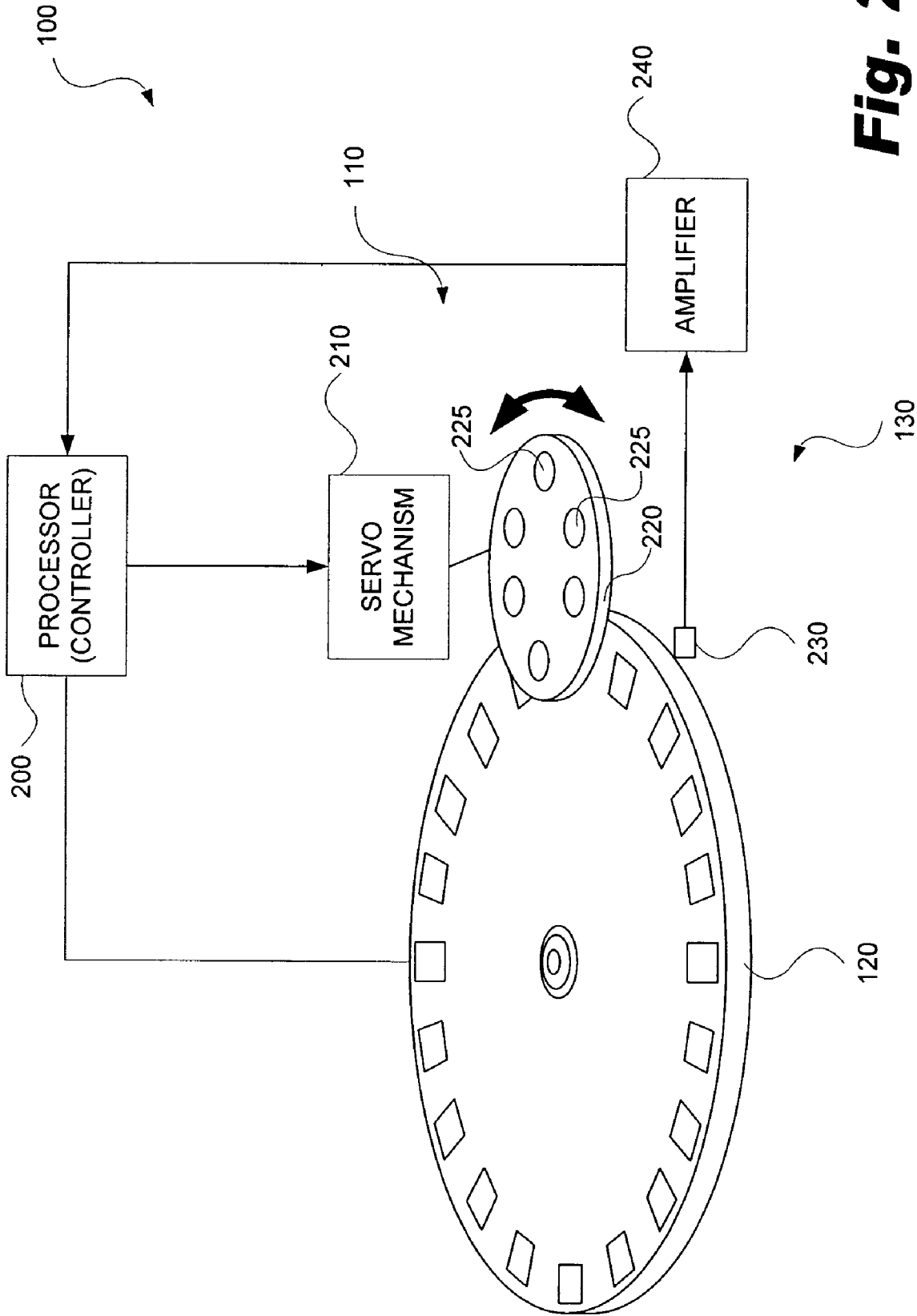
FIG. 2a illustrates a perspective view of a fluid analysis system, according to one exemplary embodiment.

FIG. 2a illustrates a detailed perspective view of a fluid analysis system, according to one exemplary embodiment. A number of system components are detailed in FIG. 2a. As shown, the exemplary fluid analysis system (100) includes a light and wavelength selection system (110) including a light generating carousel (220) having a plurality of single-wavelength light sources (225) coupled thereto. Additionally, a servo mechanism (210) may be operationally coupled to the light carousel (220). Further, a processor (200) may be controllably coupled to the servo mechanism (210), according to one exemplary embodiment. Also illustrated in the exemplary fluid analysis system (100) of FIG. 2a, an analyte-containing fluid may be presented to the light and wavelength selection system (110) by a sample presentation system (120) such as a biofluid coupon with cuvettes about the perimeter. Moreover, as shown in FIG. 2a, the analyte detection system (130) may include an optical sensor (230) communicatively coupled to an amplifier (240) and to the processor (200). Further details of the exemplary fluid analysis system (100) will be provided in detail below.

As shown in FIG. 2a, the combination light source and wavelength selection system (110) may include a number of components including, but in no way limited to, a processor (200), a servo mechanism (210), and a light generating carousel (220). According to one exemplary embodiment illustrated in FIG. 2a, the light generating carousel (220) may comprise a substantially disk shaped support member having a plurality of single-wavelength light sources (225) coupled to the perimeter thereof. According to one exemplary embodiment, the disk shaped support member hosting the plurality of single-wavelength light sources (225) may be formed of any number of materials including, but in no way limited to, a metal, a polymer, and/or a composite.

According to the illustrated embodiment, the light generating carousel (220) may include any number of single-wavelength light sources (225) that may be selectively oriented to illuminate a desired analyte. According to one exemplary embodiment, the single-wavelength light sources (225) may be any number of single-wavelength light sources including, but in no way limited to, light emitting diodes (LEDs) and/or micro-lasers. LEDs are extremely durable, having lifetimes in the tens of thousands of hours. Use of the selectively oriented single-wavelength light sources allows the light generating carousel (220) to be designed to provide illumination in any number of desired wavelengths to a desired analyte-containing region on the sample presentation system (120).

According to one exemplary embodiment, the light generating carousel (220) may include an array of individual LEDs that emit light ranging in wavelength from 350 to 960 nm. According to one exemplary embodiment, the mentioned wavelength range may be accomplished with a carousel of LEDs. Consequently, coverage of the visible spectrum, plus near UV and near IR, where the vast majority of common analytes, tagged, and un-tagged chromophores display absorption or emission features, may be accomplished at lower costs than traditional light sources.

According to the exemplary embodiment illustrated in FIG. 2a, the light generating carousel (220) may be disposed adjacent to the sample presentation system (120) in a generally parallel plane as the sample presentation system. As shown, the rotational axes of the sample presentation system (120) and the light generating carousel (220) are substantially parallel and offset such that the outer edges of the sample presentation system and the light generating carousel (220) are slightly overlapped. As illustrated, the single-wavelength light sources (225) may be selectively rotated to be disposed above the sample presentation system (120). Consequently, the single-wavelength light sources (225) of the light generating carousel (220) generate a desired wavelength of light that may then be passed through an analyte-containing fluid contained on the sample presentation system (120), such as a micro-fluidic disk, and onto the optical sensor (230). According to the exemplary embodiment illustrated in FIG. 2a, the light generating carousel (220) rotates the appropriate single-wavelength light source (225), such as an LED, into position. This allows light with a wavelength characteristic substantially matching that of an absorption or emission feature of the analyte-containing solution of interest to pass through the sample of analyte contained in the micro-fluidic disk (120). The ability to selectively rotate the light generating carousel (220) provides the ability to measure many analyte-containing solutions that require different illumination wavelengths to match their absorption or emission spectra on a single sample presentation system (120) such as a micro-fluidic disk.

Figure 2B:
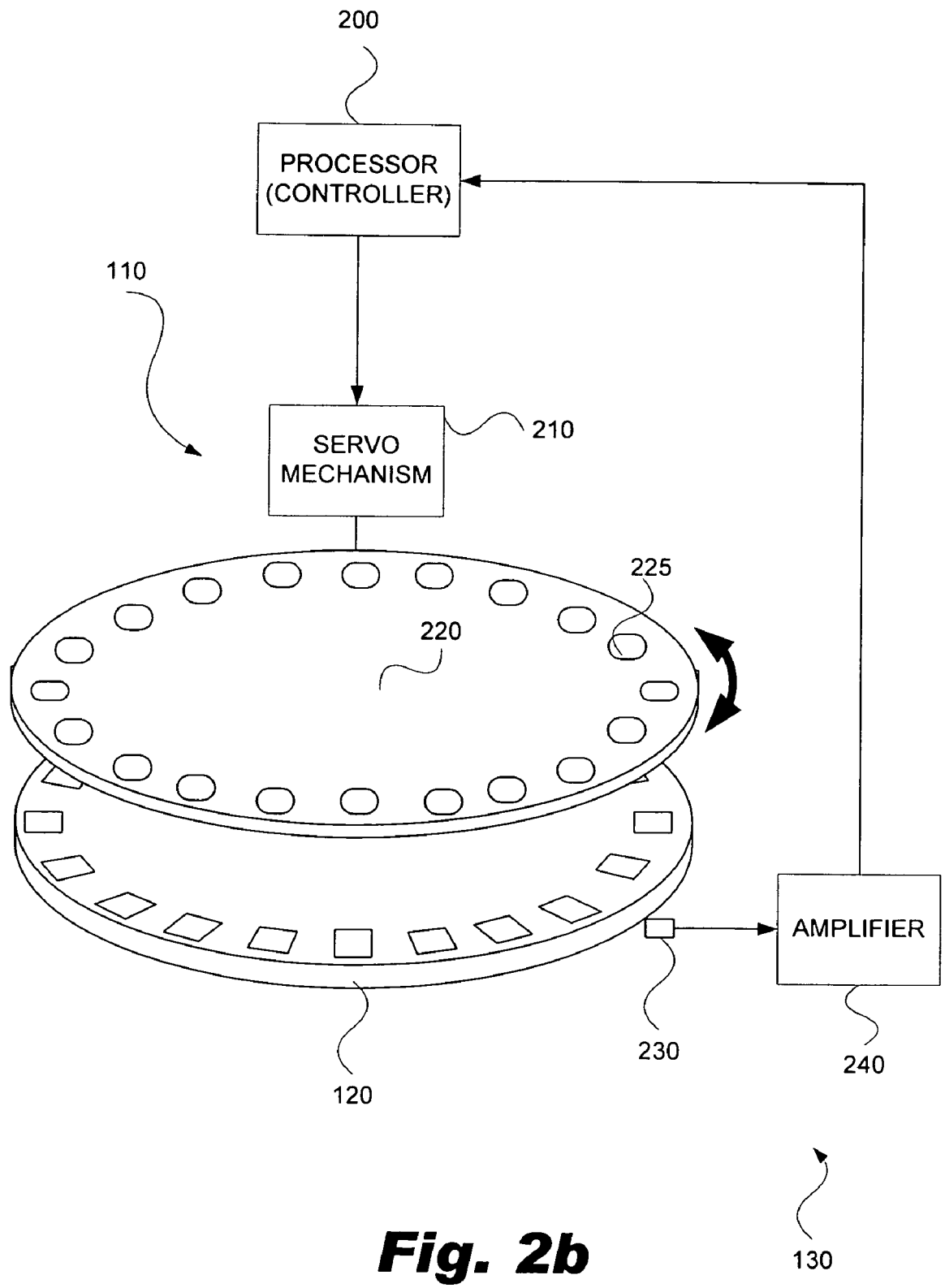
FIG. 2b illustrates a perspective view of a fluid analysis system, according to one exemplary embodiment.

While the light generating carousel (220) in FIG. 2a is illustrated as a disk shaped member having a number of single-wavelength light sources (225) disposed around the periphery thereof, the light generating carousel (220) may assume any number of shapes and/or configurations. FIG. 2b illustrates a light generating carousel configuration including a light generating carousel having a plurality of single-wavelength light sources (225) disposed on the periphery thereof. As illustrated in FIG. 2b, the axis of the light generating carousel (220) is concentric with the axis of the sample presentation system (120) having multiple sources. As shown, there is a one to one correspondence between the multiple light sources (225) and the cuvettes. Consequently, rotation of either the light generating carousel (220) and/or the sample presentation system (120) could rapidly expose various cuvettes to different light source combinations.

Additionally, FIGS. 3a and 3b illustrate two alternative light generating carousel shapes. As illustrated in FIG. 3a, the light generating carousel (300) may include a disk shaped member (310) with a number of single-wavelength light sources (225) disposed on the outer periphery thereof such that the single-wavelength light sources may emit light in a radial direction from the disk shaped member (310). According to this exemplary embodiment, the light generating carousel (300) may be selectively rotated from an axis at the center of the disk (330), as illustrated by the arrow in FIG. 3a. According to one exemplary configuration, the light generating carousel (300) may be oriented perpendicular to a sample presentation system (120) such as a micro-fluidic disk containing a desired analyte. According to this exemplary embodiment, the light generating carousel (300) may be selectively rotated to provide a desired single-wavelength light source (225) adjacent to the desired analyte-containing region for analysis.

Alternatively, the light generating member may assume a non-disk shape as illustrated in FIG. 3b. According to this exemplary embodiment, the light generating member (350) may include a polygonal shaped member (360) having a number of single-wavelength light sources (225) disposed thereon in a substantially linear array. According to this exemplary embodiment, the polygonal shaped light generating member (350) may be linearly translated, as indicated by the arrow of FIG. 3b, to selectively dispose the single-wavelength light source (225) adjacent to a desired analyte-containing region. According to one exemplary embodiment, the polygonal shaped light generating member may be oriented tangential to the outer periphery of a disk shaped sample presentation system (120). Alternatively, the polygonal shaped light generating member (350) may be associated with sample presentation systems (120) of various shapes, including, but in no way limited to a polygonal shaped sample presentation system (120).

Returning again to FIG. 2a, the light and wavelength selection system (110) also includes a servo mechanism (210) configured to selectively orient the single-wavelength light sources (225) adjacent to the sample presentation system (120). According to one exemplary embodiment, the servo mechanism (210) may include any number or combination of a stepper/servo motor system, a shaft system, a belt system, a gear system, and the like. More specifically, the servo mechanism (210) incorporated by the light and wavelength selection system (110) may be rotational and/or translational to correspond with the sample presentation device (120). Use of the servo mechanism in conjunction with a light generating carousel provides testing speed, accuracy, and functionality.

The processor (200) that is controllably coupled to the servo mechanism (210), shown in FIG. 2a, may be configured to control the selective positioning of the light generating carousel (220) relative to the analyte position of the sample presentation system. According to one exemplary embodiment, a desired light source (225) configured to generate a desired wavelength, corresponding to an analyte, may be identified using a program hosted by the processor (200). That identified light source (225) may then be converted into servo instructions that are then housed in a processor readable medium (not shown). When accessed by the processor (200), the instructions housed in the processor readable medium may be used to control the servo mechanisms (210), thereby selectively positioning the light generating carousel (220). The processor (200) illustrated in FIG. 2a may be, but is in no way limited to, a micro-controller, a workstation, a personal computer, a laptop, a personal digital assistant (PDA), or any other processor containing device.

Continuing with FIG. 2a, an exemplary sample presentation system (120) is illustrated in the form of a biofluid coupon with cuvettes about the perimeter. While a disk-shaped biofluid coupon is illustrated as an exemplary sample presentation system (120) in FIG. 2a, any number of sample presentation systems having various geometries may be incorporated in the present exemplary fluid analysis system (100). Specifically, the sample presentation system may be rectangular, elliptical, circular, or any other geometry, as is known in the art. According to the exemplary embodiment illustrated in FIG. 2a, the disk shape biofluid coupon with cuvettes located about the perimeter, configured to function as a sample presentation system (120) may include a circular disk disposed on a rotating central spindle, or alternatively, the sample presentation system may include a rectangular coupon which may have one or two axis linear motion. According to the exemplary embodiment illustrated in FIG. 2a, the sample presentation system (120) may also be controllably coupled to the processor (200) for controlling movement thereof.

According to one exemplary embodiment, the sample presentation system (120) may include cuvettes for housing the desired analyte-containing fluid. According to this exemplary embodiment, the cuvettes may be glass or plastic vials with flat smooth sides that permit absorbance measurements on the contents of the vial. According to one exemplary embodiment, the disk may be made from transparent polymethylmethacrylate. The volume of the vial may vary including volumes in the tens of microliters and even to as low as the single microliter range or less. Additionally, the sample presentation system (120) may include any number of microfluidic coupons with capillary or pneumatic channels for moving fluids. Further, the sample presentation system (120) may include any number of mechanisms, channels, active valves, passive valves, syringes, and or pipettes configured to aid in the mixing or dilution of the desired analyte-containing solution with reagents.

According to one exemplary embodiment, the sample presentation system (120) may include a rotating disk containing micro-fluidic channels where chemical reactions involving the analyte may be performed by inertial mixing etc. Additionally, a counter-rotating light generating carousel (220) containing an array of LEDs or other identified light source (225) located at the periphery may be disposed just above the micro-fluidic disk and slightly overlapping it. At the periphery of the sample presentation system disk (120) are located "cuvettes" where the isolated analyte or chromophore containing solution may be located. Directly above an identified "cuvette" would be the LED or other light source (225) of the appropriate wavelength, its light passing through the cuvette and onto an analyte detection system (130). According to this exemplary embodiment, the light generating carousel (220) rotates the appropriate light source (225) into position. This allows light with a wavelength characteristic substantially matching that of an absorption or emission feature of the analyte-containing solution of interest to pass through the sample of analyte contained in the micro-fluidic disk (120). This light generating carousel (220) provides the fluid analysis system (100) with the ability to measure a panel of analytes that each require a different wavelength to match their absorption or emission spectra, on a single sample presentation system (120).

Continuing with FIG. 2a, a signal detection system (130) is also associated with the present fluid analysis system (100). According to one exemplary embodiment, the signal detection system (130) may include an optical sensor (230) communicatively coupled to a signal amplifier (240). The signal detection system (130) is configured to sense characteristics of analytes or analyte chemical reaction products in the sample presentation system (120).

According to one exemplary embodiment, the optical sensor (230) may be any optical sensor configured to sense the characteristics of the light incident on, passing through, reflected by, or fluoresced from the analyte or analyte chemical reaction. According to one exemplary embodiment, the optical sensor (230) may include, but is in no way limited to, a photodiode, a photocell, or charge coupled device (CCD). As used herein, the term "charge coupled device" or "CCD" is meant to be understood as referring to any light-sensitive integrated circuit that stores and displays data for an image in such a way that each pixel (picture element) in the image is converted into an electrical charge, the intensity of which is related to the amount of light falling on the device. The sensitivity of available optical sensors (230) such as CCDs and photodiodes allow for analysis of analytes on the microliter volume scale, i.e. pathlengths and areas in the single millimeter range.

Further, according to one exemplary embodiment, the incorporation of a CCD device as the optical sensor (230) in the present exemplary fluid analysis system (100) allows for the possible simultaneous analysis of multiple analytes. More specifically, CCDs are configured to store and display received light in such a way that each pixel of received light is converted into an electrical charge, the intensity of which is related to the amount of light failing on the device. Consequently, a relatively large CCD may be positioned under a plurality of cuvettes to simultaneously receive light associated with multiple analytes. The CCD or other optical sensor (230) may also be positioned away from the cuvettes and the light from multiple analytes transferred to the CCD with lenses, fiber optics, light pipes, or other mechanisms.

As mentioned, the light that reaches the optical sensor (230) passes from a light source (225), through an analyte disposed on the sample presentation system (120), to the optical sensor (230). Any number of system configurations may be used to selectively route the light from the light source (225) to the optical sensor (230). According to one exemplary embodiment, the light generating carousel (220) containing a number of single-wavelength light sources (225) selectively positions the single-wavelength light sources such that the light may pass through the desired analyte and on to an optical sensor without the use of additional optical components.

Figure 4:
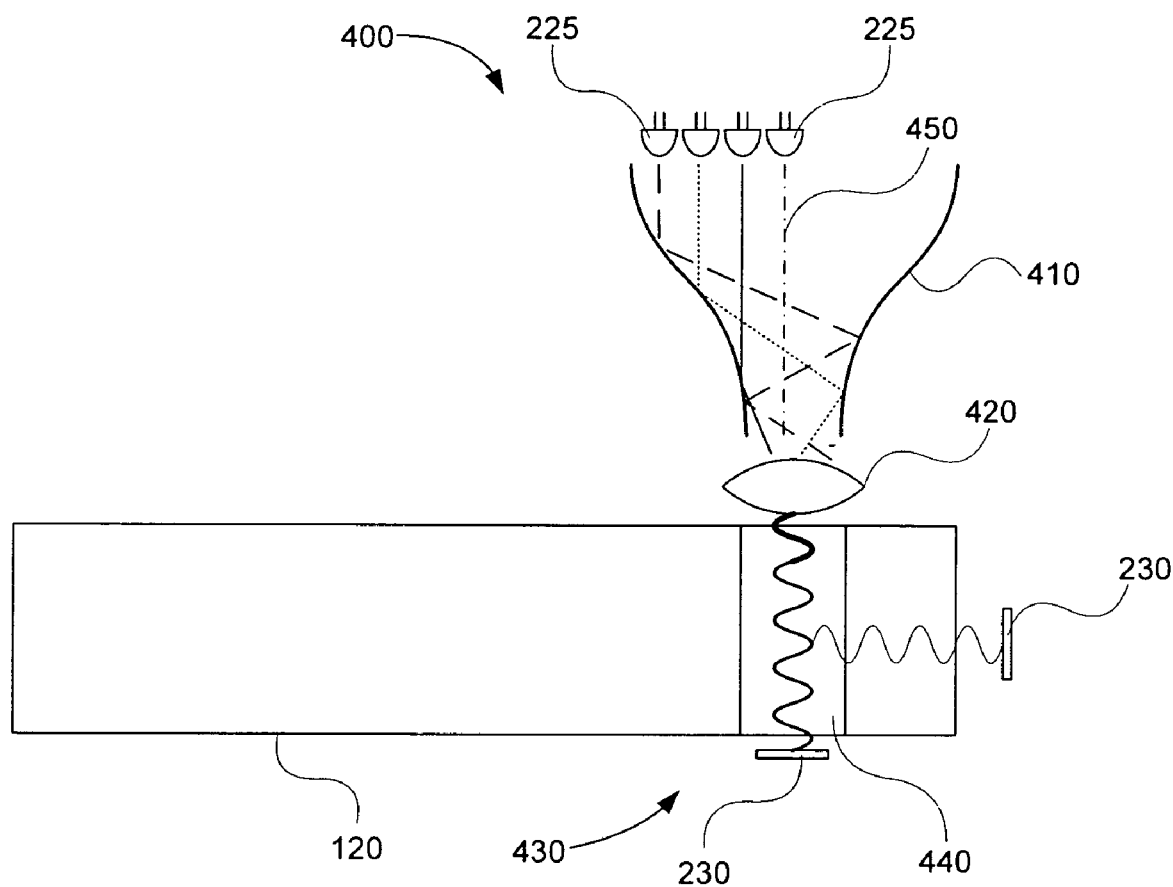
FIG. 4 illustrates a side view of a micro-fluidic coupon being analyzed, according to one exemplary embodiment.
Figure 5:
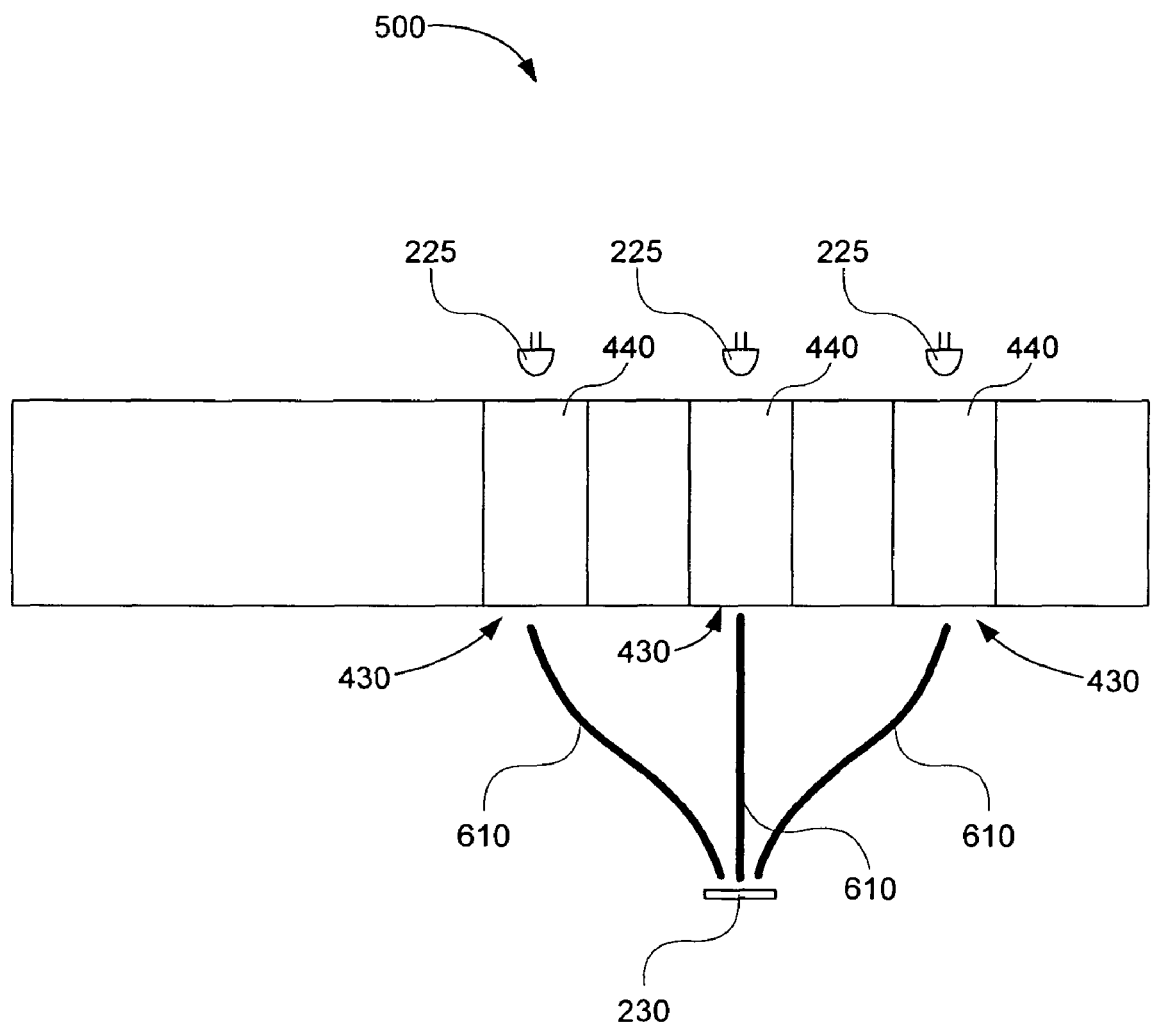
FIG. 5 illustrates a side view of a light delivery system configuration, according to one exemplary embodiment.

Alternatively, as illustrated in FIG. 4, an optical configuration (400) may include a number of single-wavelength light sources (225), such as LEDs, linearly arranged over a measurement zone such as an analyte or analyte-derived chromophore (440) contained in a cuvette (430). Since each single-wavelength light source (225) is focused onto the cuvette and the signal collected by the photodetector for analyte testing, the single-wavelength light sources (225) may be channeled. As illustrated in FIG. 4, the single wavelength light (450) generated by the single-wavelength light source (225) may be channeled to a single emission zone with the use of a lightpipe (410). According to one exemplary embodiment, the lightpipe (410) may include any number of hollow cylinders having a substantially reflective inner surface or optical fiber having a high degree of total internal reflection. Additionally, as illustrated in FIG. 4, the exemplary optical configuration (400) may include any number of focusing optics (420) configured to focus the generated single-wavelength light (450). Once the single-wavelength light (450) has been channeled to an analyte, the light goes through the analyte and excites an analyte or chromophore, such as fluorophore, and the subsequent emission of light is detected perpendicular to the incoming light to maximize the desired signal relative to incident and stray light.

Figure 6:
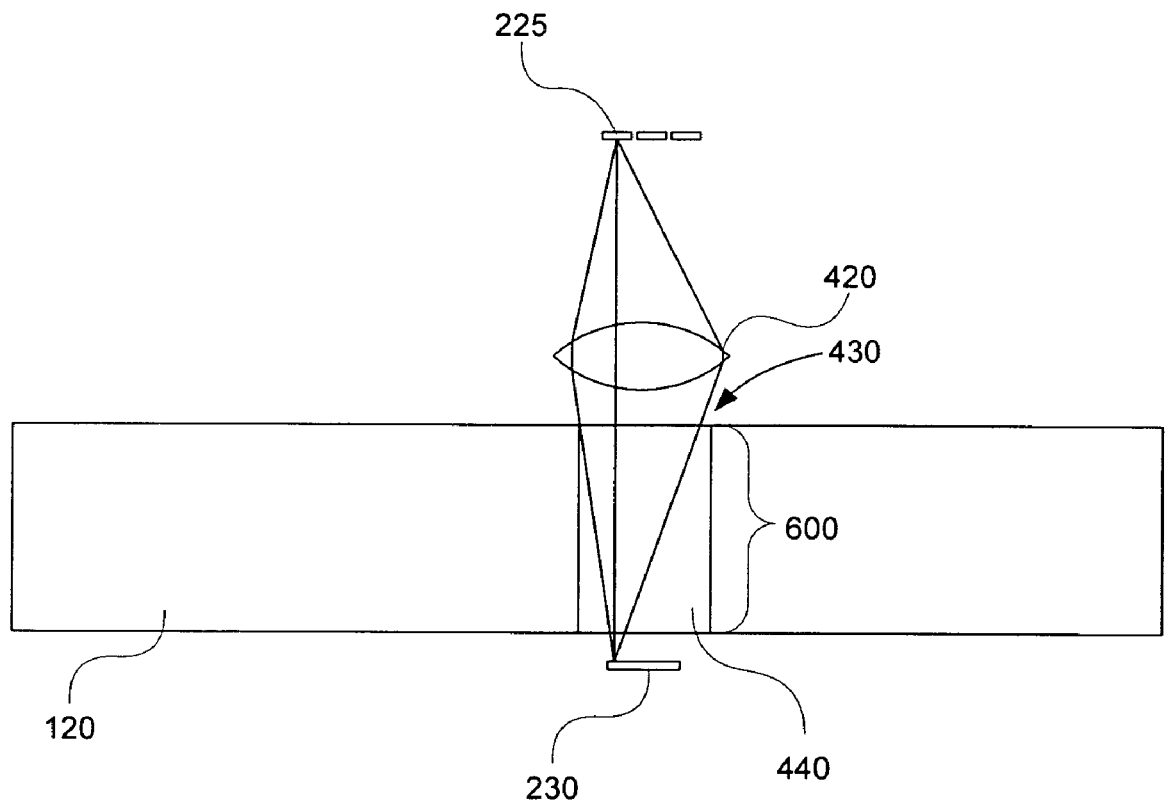
FIG. 6 illustrates a side view of a light delivery system configuration, according to one exemplary embodiment.

Alternatively, an exemplary fluid analysis system (500) illustrated in FIG. 6 shows the single-wavelength light sources (225) may be arrayed above a plurality of cuvettes (430) containing a desired analyte or analyte-derived chromophore (440). According to this exemplary embodiment, the signals passing through the analytes or chromophores (440) of the various cuvettes (430) are then routed to the photodetector by individual optical fibers (610). According to this exemplary embodiment, the individual sources (225) may be selected to provide optical communication between the desired single-wavelength light sources (225) and the optical sensor (230).

Regardless of the method of routing the single wavelength light to the optical sensor (230), the optical sensor may be configured to detect any number of wavelength characteristics of the analyte or analyte-derived chromophore including, but in no way limited to, absorption or emission, fluorescence, chemiluminescence, and combinations thereof. Positioning the detector perpendicular to the incoming light is often preferred for sensitive fluorescence and chemiluminescence measurements. Detectors used in this mode may require filtering for optimal signal quality, as illustrated in FIG. 4. Regardless of the optical sensor incorporated into the exemplary fluid analysis system (400), the detection of light by the optical sensor (230) is converted into an electrical charge. The weak electrical charge generated by the optical sensor (230) may then be passed through a signal amplifier (130) before being transmitted to the processor (200), as illustrated in FIGS. 2a and 2b.

Once received by the processor, the electrical signal may then be analyzed for wavelength characteristics of the analyte reaction chemistry. According to one exemplary embodiment illustrated in FIG. 6, the absorbance of a desired analyte reaction chemistry may be determined according to Beer's Law as illustrated by the following formula:

$$A = \square bc \qquad \text{Formula 1}$$

Where the absorbance (A) equals the molar extinction coefficient ($\square$) multiplied by the absorption or emission path length (b) and the chromophore concentration (c). As illustrated in FIG. 6, the absorption or emission path length (600) of the analyte or analyte-derived chromophore (440) may be known according to the size of the cuvette (430). Additionally, the extinction coefficient ($\square$) of the analyte or analyte-derived chromophore may be ascertained by the processor (200; FIG. 2a) from a lookup table, according to one exemplary embodiment. Once the above-mentioned characteristics are determined and/or measured, the concentration (c) of the analyte may be computed. An exemplary method for operating the above-mentioned exemplary fluid analysis system (100) will now be described in further detail below.

Exemplary Operation

Figure 7:
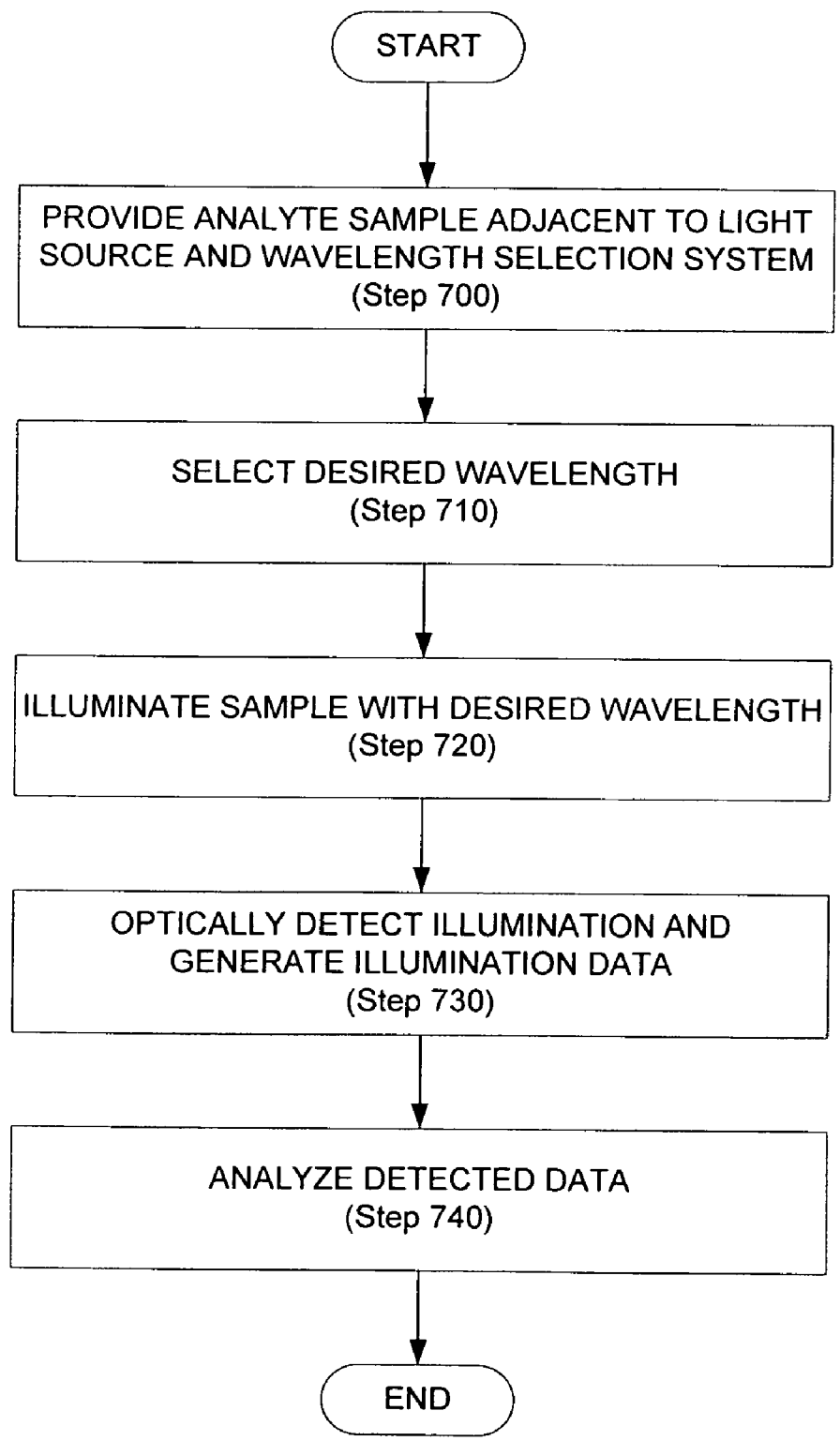
FIG. 7 is a flow chart illustrating a method for analyzing a fluid with a fluid analysis system, according to one exemplary embodiment.

FIG. 7 illustrates an exemplary method for using the above-mentioned fluid analysis system (100), according to one exemplary embodiment. As illustrated in FIG. 7, the present exemplary method begins by first providing an analyte sample adjacent to the light source and wavelength selection system (step 700). The analyte sample may be provided adjacent to the light source and wavelength selection system (110; FIG. 1) in any number of forms and using any number of analyte presentation devices. According to one exemplary embodiment, the analyte sample may be provided adjacent to the light source and wavelength selection system using a biofluid coupon with cuvettes formed about the perimeter.

Figure 8:
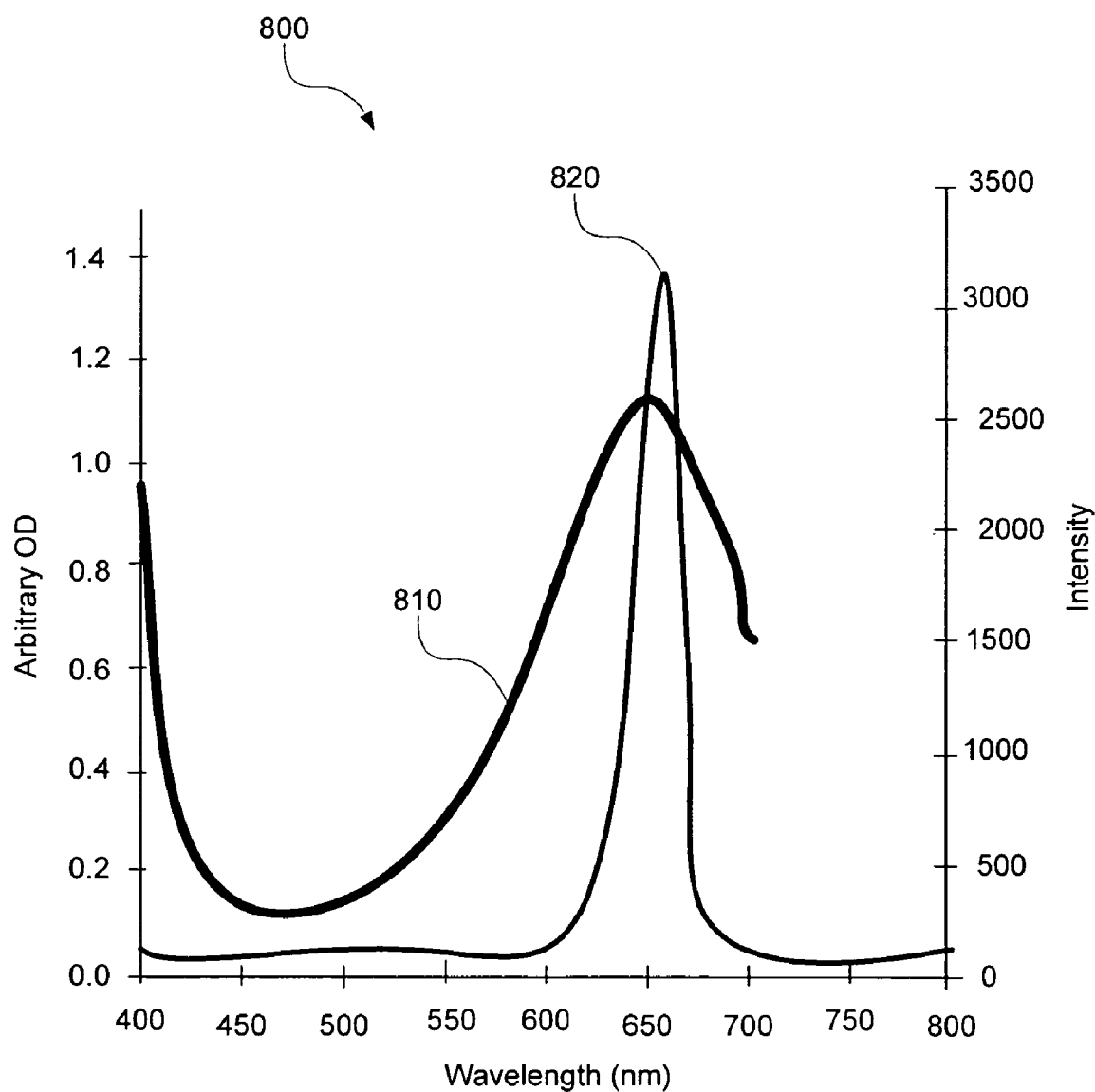
FIG. 8 is a chart illustrating an analyte absorption or emission spectra and a corresponding emission spectrum of a single-wavelength light source according to one exemplary embodiment.

Once the desired analyte is disposed adjacent to the light source and wavelength selection system (step 700), a desired wavelength may be selected (step 710). According to the present exemplary embodiment, the desired wavelength for the single-wavelength light source may be selected based, at least in part, on the anticipated absorption or emission spectra of the analyte reaction chemistry of the analyte being tested. As illustrated in FIG. 8, an absorption or emission spectra is displayed (800) illustrating the characteristics of both an analyte (810) and a single-wavelength light source (820). As illustrated in FIG. 8, the analyte absorption or emission spectrum includes at least one peak. Similarly, the LED emission spectrum (820) exhibits a peak associated with its radiation wavelength. As shown in FIG. 8, one particular light source may exhibit an emission peak corresponding with peaks in the analyte absorption or emission spectrum.

Continuing with the exemplary method of FIG. 7, with the desired wavelength identified (step 710), the sample analyte or analyte reaction chemistry may then be illuminated by a single-wavelength light source radiating the identified wavelength (step 720). More particularly, according to one exemplary embodiment, once the desired wavelength is identified by the processor (200; FIG. 2a) or the operator, the light generating carousel (220) may be controllably maneuvered, via the servo mechanism (210), to orient a desired single-wavelength light source (225) adjacent to the provided analyte. The single-wavelength light source (225) may then be controllably illuminated to pass a desired wavelength of light through the provided analyte.

As the analyte or analyte reaction chemistry is illuminated, light that traverses the solution may then be optically detected by the photodetector (230; FIG. 2a) and used to generate illumination data (step 730). Once the illumination data is generated, the data may be amplified and transmitted to a processor for analysis (step 740). As mentioned previously, the generated illumination data may be analyzed for any number of characteristics including, but in no way limited to, absorption or emission according to Beer's Law, as described in detail above.

In conclusion, the present exemplary system and method provide a simple robust optical analysis system that reduces cost while maintaining utility and speed. More specifically, according to one exemplary embodiment, the present multi-wavelength selector structure includes multiple single-wavelength light sources such as light emitting diodes (LEDs) or lasers, which may assume any number of structural configurations, focusing or channeling to a small area. Additionally, as mentioned above, the incorporation of multiple single-wavelength light sources, in conjunction with a photodetector such as a CCD or photodiode allows multiple analytes to be measured simultaneously.

The preceding description has been presented only to illustrate and describe the present method and apparatus. It is not intended to be exhaustive or to limit the disclosure to any precise form disclosed. Many modifications and variations are possible in light of the above teaching. It is intended that the scope of the disclosure be defined by the following claims.

What is claimed is:

1. A method of using a light source carousel including a plurality of selectable single-wavelength light sources, comprising:
    selecting a desired single-wavelength light source from said plurality of selectable single-wavelength light sources;
    illuminating an analyte with said desired single-wavelength light source; and
    detecting a wavelength associated with said analyte when illuminated by said selected single-wavelength;
    said selecting of the desired single-wavelength light source being accomplished by rotating said carousel which supports said plurality of single-wavelength light sources so as to optically couple one of said light source with said analyte, and rotating a micro-fluidic disk bearing said analyte to position said analyte for illumination;
    wherein said carousel bearing said light sources and said micro-fluidic disk are concentric and rotate on a common axis.

2. The method of claim 1, wherein said selecting a desired single-wavelength light source from said plurality of selectable single-wavelength light sources is at least partially based on an absorption or emission characteristic of said analyte.

3. The method of claim 1, wherein said selecting a desired single-wavelength light source from said plurality of selectable single-wavelength light sources comprises:
    identifying a peak or plateau in an absorption or emission spectrum of said analyte; and
    selecting a single-wavelength light source with a radiation wavelength associated with said absorption or emission spectrum peak or plateau.

4. The method of claim 1, further comprising:
    illuminating a plurality of analytes simultaneously with said plurality of selectable single-wavelength light sources; and
    simultaneously detecting wavelengths associated with said plurality of illuminated analytes.

5. The method of claim 4, wherein said simultaneously detecting wavelengths associated with said plurality of illuminated analytes comprises detecting said wavelengths with a charge coupled device.

6. The method of claim 1, wherein there is a one-to-one correspondence between said plurality of light sources and cuvettes on said micro-fluidic disk.

7. The method of claim 1, further comprising additionally rotating said carousel to optically couple said analyte to a series of said light sources, in which said light sources emit different wavelengths of light.

8. The method of claim 1, wherein selecting a desired single-wavelength light source comprises translating a substrate bearing said plurality of light sources with respect to said analyte so as to optically couple a selected light source with said analyte.

9. The method of claim 1, further comprising using a light pipe to optically couple said plurality of light sources with said analyte.

10. A method of using a light source carousel including a plurality of selectable single-wavelength light sources to analyze number of analytes, said method comprising:
    rotating said carousel which supports said plurality of single-wavelength light sources so as to optically couple one of said light sources with said analytes;
    rotating a micro-fluidic disk bearing said analytes in a number of cuvettes defined in the micro-fluidic disk to position said analytes for illumination;
    illuminating said analytes with said optically coupled light source; and
    detecting light from said illuminated analytes,
    in which there is a one-to-one correspondence between said plurality of light sources and cuvettes on said micro-fluidic disk.

11. The method of claim 10, wherein said carousel bearing said light sources and said micro-fluidic disk are concentric and rotate on a common axis.

12. The method of claim 10, further comprising additionally rotating said carousel to optically couple said analyte to a series of said light sources, in which said light sources emit different wavelengths of light.

13. The method of claim 10, wherein detecting light from said illuminated analyte further comprises detecting analyte chemical reaction products in said sample of said analyte.

* * * * *